United States Patent [19]

Hickey et al.

[11] Patent Number: 5,321,163

[45] Date of Patent: Jun. 14, 1994

[54] MULTI-PURPOSE CATALYTIC DISTILLATION COLUMN AND ETERIFICATION PROCESS USING SAME

[75] Inventors: Thomas P. Hickey, Houston; John R. Adams, Pasadena, both of Tex.

[73] Assignee: Chemical Research & Licensing Company, Pasadena, Tex.

[21] Appl. No.: 118,311

[22] Filed: Sep. 9, 1993

[51] Int. Cl.$^5$ .................. C07C 319/16; C07C 41/06
[52] U.S. Cl. .......................... 568/59; 568/60; 568/697; 568/38
[58] Field of Search ................. 568/59, 60, 579, 38, 568/697

[56] References Cited

U.S. PATENT DOCUMENTS

| | | | |
|---|---|---|---|
| 2,717,202 | 9/1955 | Bailey | 23/283 |
| 3,186,935 | 6/1965 | Vaell | 208/59 |
| 3,531,542 | 2/1970 | Myers et al. | 260/683.2 |
| 3,839,486 | 1/1974 | Arganbright | 260/683.2 |
| 4,003,829 | 1/1977 | Burger et al. | 208/253 |
| 4,213,847 | 7/1980 | Chen et al. | 208/111 |
| 4,221,653 | 9/1980 | Chervenak et al. | 208/8 LE |
| 4,307,254 | 12/1981 | Smith, Jr. | 568/693 |
| 4,336,407 | 6/1982 | Smith, Jr. | 568/693 |
| 4,361,422 | 11/1982 | Derrien et al. | 44/51 |
| 4,439,350 | 3/1984 | Jones, Jr. | 502/527 |
| 4,443,559 | 4/1984 | Smith, Jr. | 502/527 |
| 4,490,481 | 12/1984 | Boitiaux et al. | 502/330 |
| 4,533,779 | 8/1985 | Boitiaux et al. | 585/255 |
| 4,550,012 | 10/1985 | Penick | 422/106 |
| 4,709,115 | 11/1987 | Jung et al. | 585/643 |
| 5,087,780 | 2/1992 | Arganbright | 585/259 |
| 5,196,612 | 3/1993 | Ward | 568/697 |

FOREIGN PATENT DOCUMENTS

| | | |
|---|---|---|
| 87980 | 9/1983 | European Pat. Off. . |
| 835689 | 2/1960 | United Kingdom . |
| 920012 | 3/1963 | United Kingdom . |
| 1205677 | 9/1970 | United Kingdom . |

OTHER PUBLICATIONS

Boitiaux, et al, "Newest Hydrogenation Catalysts," *Hydrocarbon Processing*, Mar. 1985 pp. 51-59.

Buselli, A. J., "Butene-1 to Polybutene-Economic Outlook & Prospects," Abstract of Paper Presented to Division of Petroleum Chemistry, ACS, Mar. 1978.

Heck et al "Catalytic Processes Using $C_4$ Streams for Octane Improvement: Hydro-Isomerization and MTBE," Paper Presented to Division of Petroleum Chemistry, Inc. AC; mar. 1980.

Derrien, et al "The IFP Selective Hydrogenation Process," *Chemical Engineering Progress*, Jan. 1974 pp. 74-80.

*Primary Examiner*—James H. Reamer
*Assistant Examiner*—Margaret J. Page
*Attorney, Agent, or Firm*—Kenneth H. Johnson

[57] ABSTRACT

A multi-purpose distillation column reactor is disclosed which may be used for the production of tertiary amyl methyl ether from the reaction of the isoamylenes contained in a light naphtha with methanol. Two reaction distillation zones are disposed above a stripping section. The stripping, in addition to removing the TAME product, also removes the $C_6$ and heavier components. The first reaction distillation zone contains a hydrotreating catalyst for removing diolefins and mercaptans. The second distillation reaction zone contains an acid cation exchange resin for the etherification reaction and the entire column serves to fractionate the multiple component reaction system (reacts, inerts, products and contaminants) concurrently with the multiple reactions.

4 Claims, 1 Drawing Sheet

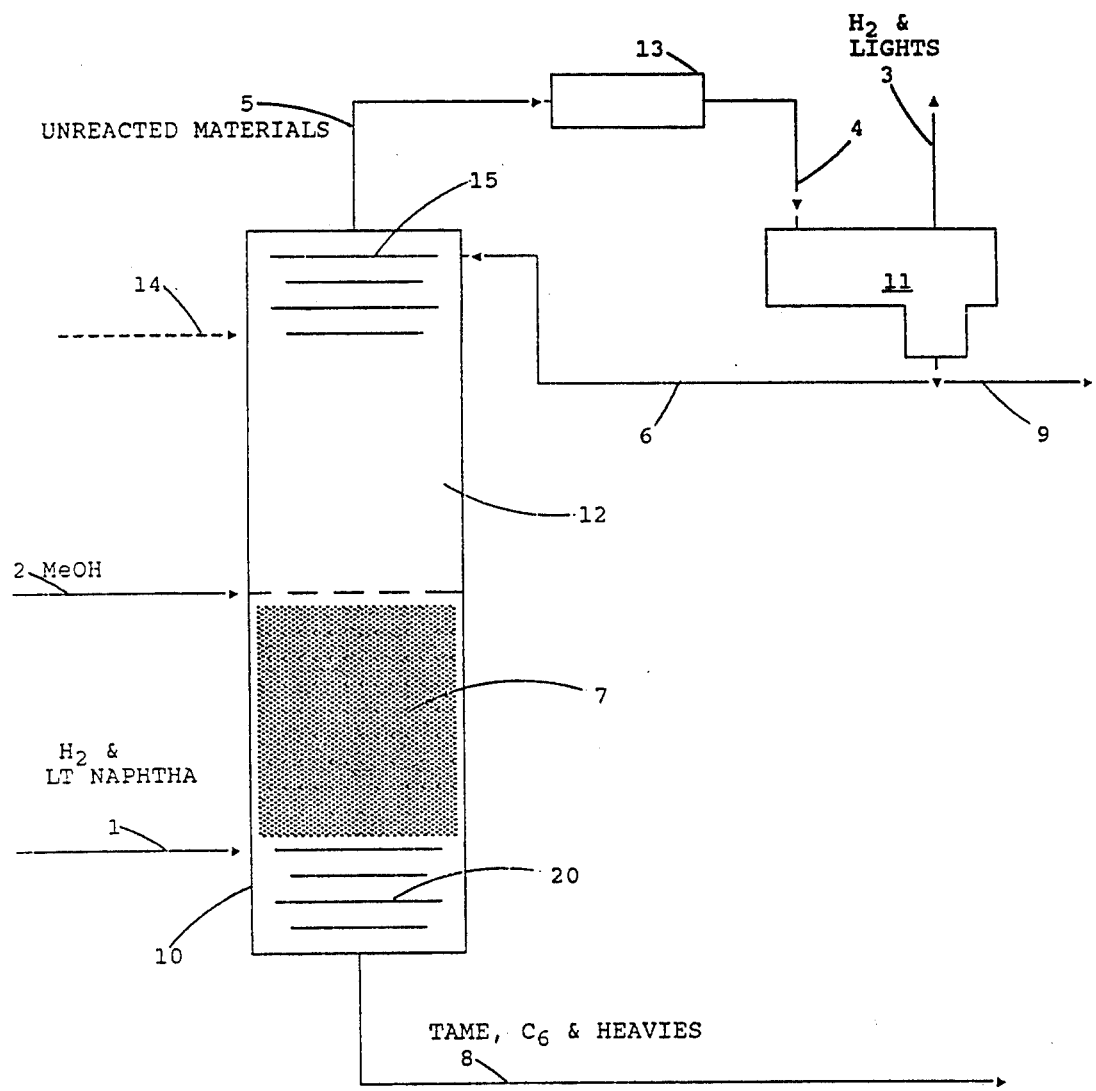

MULTI-PURPOSE CATALYTIC DISTILLATION COLUMN AND ETERIFICATION PROCESS USING SAME

BACKGROUND OF THE INVENTION

1. Field of the Invention

The present invention relates to a multi-purpose catalytic distillation column and the use of the column to produce an ether from the reaction of an isoolefin with an alcohol. More particularly the invention relates to the production of tertiary amyl methyl ether by the reaction of the isoamylenes contained within a cracked naphtha stream with methanol in a distillation column reactor which removes the $C_6+$ fraction, sweetens the feed by removing mercaptans, removes the nitriles in the feed, selectively hydrogenates the dienes in the feed and reacts the isoamylenes with methanol to produce tertiary amyl methyl ether.

2. Related Art

The $C_5$ refinery cut is valuable as a gasoline blending stock or as source of isoamylene to form an ether by reaction with lower alcohols. Tertiary amyl methyl ether (TAME) is rapidly becoming valuable to refiners as a result of the recently passed Clean Air Act which sets some new limits on gasoline composition. Some of these requirements are (1) to include a certain amount of "oxygenates", such as methyl tertiary butyl ether (MTBE), TAME or ethanol, (2) to reduce the amount of olefins in gasoline, and (3) to reduce the vapor pressure (volatility).

In most $C_5$ cuts the isoamylene suitable for the production of TAME is frequently present in small quantities, e.g. less than 15%, whereas there are other $C_5$ olefin isomers and enough dienes and acetylenes to inhibit the etherification process. It is an advantage of the present invention that the contaminants such as the diolefins, acetylenes, mercaptans and nitriles are removed before the etherification in the single distillation column reactor. It also an advantage that the stream recovered from the column containing the ether is suitable without further treatment to be used as an octane blending stock. These and other advantages and features of the present invention become clear from the following descriptions.

SUMMARY OF THE INVENTION

Briefly the present invention comprises a single distillation column reactor wherein a cracked light naphtha stream is fed to produce tertiary amyl methyl ether. The distillation column reactor acts as a depentanizer to remove the $C_6$ and heavier fraction and because methanol is fed at the same time an azeotropic separation of the nitriles from the $C_5$ portion is effected. Suitable beds of catalytic distillation structure are arranged to achieve all of the desired reactions. A first bed selectively reacts some of the diolefins with mercaptans to produce heavier materials which can be removed with the $C_6$ bottoms and selectively hydrogenates the diolefins in the feed and a second bed performs the etherification function.

The preferred process of the invention for the production of tertiary amyl methyl ether comprising the steps of:

(a) feeding a first stream comprising a light cracked naphtha to a distillation column reactor having a stripping section and a first distillation reaction zone containing a hydrogenation catalyst in the form of a catalytic distillation structure and a second distillation reaction zone containing an acid cation exchange resin in the form of a catalytic distillation structure;

(b) concurrently feeding a second stream containing hydrogen and a third stream containing methanol to said distillation column reactor;

(c) separating the $C_6$ and heavier boiling fraction from said light cracked naphtha in said stripping section while boiling the $C_5$ fraction up into said first distillation reaction zone;

(d) concurrently in said first distillation reaction zone:

(i) removing sulfur compounds, which are primarily mercaptans by reacting the mercaptans contained within said $C^5$ boiling fraction with a portion of the diolefins contained within said $C_5$ boiling fraction to produce sulfides having a boiling range higher than said $C_5$ boiling fraction;

(ii) reacting the remainder of the diolefins and any acetylenes contained within said $C_5$ boiling fraction with a portion of said hydrogen to reduce the unsaturation and isomerizing a portion of isoolefins; and (iii) forming a $C_5$/methanol azeotrope and boiling said azeotrope up into said second distillation reaction zone while separating said sulfides and any nitrogen containing compounds contained within said $C_5$ fraction by fractional distillation;

(e) concurrently in said second distillation reaction zone:

(i) reacting the isoamylenes contained within said azeotrope with methanol contained said azeotrope to form tertiary amyl methyl ether, and (ii) separating said tertiary amyl methyl ether from unreacted $C_5$'s and methanol by fractional distillation;

(f) withdrawing unreacted $C_5$'s, unreacted methanol and unreacted hydrogen from said distillation column reactor as overheads; and (g) withdrawing said $C_6$ and heavier fraction, said tertiary amyl methyl ether, said sulfides and said nitrogen containing compounds from said distillation column reactor as bottoms.

The heavier boiling components of step (c) above include TAME, the sulfides and nitriles which ultimately leave the reactor column in the bottoms.

BRIEF DESCRIPTION OF THE DRAWING

The FIGURE is a simplified schematic representation of a catalytic distillation column configured for the present invention.

DETAILED DESCRIPTION OF THE PREFERRED EMBODIMENTS

The $C_5$'s in the feed to the present TAME unit are contained in a single "light naphtha" cut which may contain everything from $C_5$'s through $C_8$'s and higher. This mixture can easily contain 150 to 200 components. Mixed refinery streams often contain a broad spectrum of olefinic compounds. This is especially true of products from either catalytic cracking or thermal cracking processes. Refinery streams are usually separated by fractional distillation, and because they often contain compounds that are very close in boiling points, such separations are not precise. A $C_5$ stream, for instance, may contain $C_4$'s and up to $C_8$'s. These components may be saturated (alkanes), unsaturated (mono-olefins), or poly-unsaturated (diolefins). Additionally, the components may be any or all of the various isomers of the individual compounds. Such streams typically contain 15 to 30 weight % of the isoamylenes.

Several of the minor components (diolefins) in the feed will react slowly with oxygen during storage to produce "gum" and other undesirable materials. However, these components also react very rapidly in the TAME process to form a yellow, foul smelling gummy material. Thus it is seen to be desirable to remove these components whether the "light naphtha" cut is to be used only for gasoline blending by itself or as feed to a TAME process.

Such refinery streams also contain small amounts of sulfur and nitrogen compounds which must be removed. The sulfur compounds are generally found in a light cracked naphtha stream as mercaptans which react with the etherification catalyst to inhibit the etherification reaction. Removal of sulfur compounds is generally termed "sweetening" a stream. The nitrogen compounds normally exist as nitriles which may hydrolyze forming compounds which are basic in nature and can neutralize the acidic nature of the etherification catalyst. Thus, the removal of the mercaptans and nitriles is desirable.

The nature of sulfur compounds present is also dependent upon the boiling range of the distillate. In a light naphtha (110°-250° F. boiling range) the predominant sulfur compounds are mercaptans. Typical of the mercaptan compounds which may be found to a greater or lesser degree in a light cracked naphtha are: methyl mercaptan (b.p. 43° F.), ethyl mercaptan (b.p. 99° F.), n-propyl mercaptan (b.p. 154° F.), iso-propyl mercaptan (b.p. 135°-140° F.), isobutyl mercaptan (b.p. 190° F.), tert-butyl mercaptan (b.p. 147° F.), n-butyl mercaptan (b.p. 208° F.), sec-butyl mercaptan (b.p. 203° F.), iso-amyl mercaptan (b.p. 250° F.), n-amyl mercaptan (b.p. 259° F.), α-methylbutyl mercaptan (b.p. 234° F.), α-ethylpropyl mercaptan (b.p. 293° F.), n-hexyl mercaptan (b.p. 304° F.), 2-mercapto hexane (b.p. 284° F.), and 3-mercapto hexane (b.p. 135° F.).

Typical diolefins in the $C_5$ boiling range fraction include: isoprene (2-methyl butadiene-1,3), cis and trans piperylenes (cis and trans 1,3-pentadienes), and minor amounts of butadienes.

A suitable feed for the present invention would be a light naphtha cut comprising primarily $C_5$ hydrocarbons comprising normal alkanes, nodal alkenes, isoalkanes and isoalkenes and very minor amounts of contaminant compounds containing sulfur and nitrogen.

As described above there are concurrently at least seven functions being carried out in the catalytic distillation reactor as described, i.e.
1. etherification;
2. distillation of unreacted $C_5$ components from the etherization;
3. separation of $C_5$ components from nitrile contaminants by azeotrope distillation of the alcohol and the $C_5$'s;
4. hydrogenation of the diolefins and acetylenes;
5. removal of sulfur compounds including the reaction of mercaptans with diolefins;
6. isomerization of isoolefins;
7. distillation of $C_5$'s from the sulfides;
8. distillation of the lighter components from the ether product, the $C_6$'s and heavier hydrocarbons, nitriles and sulfides.

Referring now to the FIGURE the column and process can be understood. The distillation column reactor 10 is shown to be generally cylindrical in shape and oriented vertically. A methanol inlet 2 is provided near the lower end of zone 12. The lower portion 20 of the vessel contains inert distillation structures such as inert packing, sieve trays, bubble cap trays or the like. Section 20 is the stripping section for separating the $C_6$ and higher boiling material from the $C_5$ and lower boiling material in the light cracked naphtha. A light naphtha inlet 1 is directly above the stripping section 20. Hydrogen may be fed separately but is preferably fed with the light naphtha.

Directly above the stripping section within the column 10 is a first distillation reaction zone 7 containing hydrogenation catalyst prepared as a first catalytic distillation structure. Section 7 is the hydrogenation zone where the diolefins and acetylenes are selectively hydrogenated, mercaptans are reacted with diolefins and isoolefins are isomerized. The isomerization under the conditions of hydrogenation is of the bond type and very little, if any, skeletal isomerization occurs in the present process. The sulfides formed from the reaction of the mercaptans with the diolefins are higher boiling than the $C_5$'s and are distilled downward and removed with the bottoms.

Hydrogenation is the reaction of hydrogen with a carbon-carbon multiple bond to "saturate" the compound. This reaction is usually carried out at super atmospheric pressures and moderate temperatures using an excess of hydrogen over a metal catalyst. Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al in "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", Hydrocarbon Processing, March 1985, presents an over view of various uses of hydrogenation catalysts, including selective hydrogenation, utilizing a proprietary bimetallic hydrogenation catalyst which is also suitable in the present invention.

The reactions of interest in the first distillation zone 7 are:

(1) isoprene (2-methyl butadiene-1,3)+hydrogen to 2-methyl butene-1 and 2-methyl butene-2;

(2) cis- and trans 1,3-pentadienes (cis and trans piperylenes)+hydrogen to pentene-1 and pentene-2;

(3) 1,3-butadiene to butene-1 and butene-2, (4) 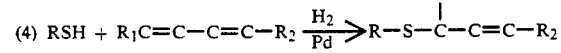

and (5) 3-methyl butene-1⇌2-methyl butene-1/2-methyl butene-2

A catalyst suitable for the hydrogenation section 7 is 0.34 wt % Pd on 3 to 8 mesh $Al_2O_3$ (alumina) spheres, supplied by United Catalysts Inc. designated as G-68C. Typical physical and chemical properties of the catalyst as provided by the manufacturer are as follows:

TABLE I

| Designation | G-68C |
| --- | --- |
| Form | Sphere |
| Nominal size | 5 × 8 mesh |
| Pd. wt % | 0.3 (0.27–0.33) |
| Support | High purity alumina |

The catalyst is believed to be the hydride of palladium which is produced during operation. The hydrogen rate to the reactor must be sufficient to maintain the catalyst in the active form because hydrogen is lost from the catalyst by hydrogenation, but kept below that which would cause flooding of the column which is understood to be the "effectuating amount of hydrogen" as that term is used herein. Generally the mole ratio of hydrogen to diolefins and acetylenes in the feed to the fixed bed of the present invention will be at least 1.0 to 1.0 preferably 2.0 to 1.0.

Other suitable catalysts for both the hydrogenation/isomerization and the etherification include a macroporous or gelatinous acid cation exchange resin in the H+ form which has been charged with a metal of group groups VI, VII or VIII of the periodic table of elements as described in U.S. Pat. No. 4,330,679.

The catalyst must be suitably supported and spaced within the column to act as a catalytic distillation structure. In the preferred embodiment the catalyst is contained in a woven wire mesh structure as disclosed in in U.S. patent application Ser. No. 901,771 filed Jun. 22, 1992 and Ser. No. 075,320 filed Jan. 15, 1993 which are hereby incorporated by reference. Other catalyst structures suitable for use in the present process are those described in U. S. Pat. Nos. 4,731,229 and 5,073,236 and European Patent No. 0396650.

Above the hydrogenation section within the column 10 the second distillation reaction zone 12 contains an acid cation exchange resin catalyst in the form of a second catalytic distillation structure. In this section 12 the isoamylenes are reacted with methanol to form tertiary amyl methyl ether (TAME) which is higher boiling than the $C_5$'s and is distilled downward and removed with the $C_6$ and heavier materials via line 8. Zone 12 may be directly above zone 7 or there may be intervening inert distillation structures (not shown) as described in zone 20.

Additionally, methanol and the $C_5$'s form an azeotrope that is lower boiling than the $C_5$'s and the nitrile contaminants. It is this azeotrope that is boiled up from the first reaction distillation zone 7 into the second reaction distillation zone 12. The isoamylenes in the azeotrope react with the methanol to form the TAME.

In the case of the $C_5$'s, the azeotrope contains about 12 wt % methanol, and the boiling point of the azeotrope is 10 to 15 degrees F. below that of the corresponding $C_5$'s. Thus, if the net flow of methanol into the column (allowing for that reacting in the column) is less than the azeotrope concentration in the distillate, the methanol concentration in the reaction distillation zone will be relatively quite low, about 1%. If the net methanol flow into the column is higher than the azeotrope, the methanol concentration will increase (60% has been measured) until methanol leaves with the TAME bottoms product. Neither case is desirable, because at low concentration the conversion of isoamylene to TAME is low, whereas at high concentrations the TAME purity is affected by the presence of the excess methanol. Thus the rate of methanol feed is constantly adjusted to maintain the amount of methanol in the column above the azeotrope but below the excess to appear in the bottoms. In one embodiment this may be adjusted by feeding a portion of the methanol above the etherification catalyst bed via line 14.

The methanol/$C_5$ azeotrope (less the nitrogen compounds and sulfides) is boiled up into the etherification section 12 which contains an acid cation exchange resin catalyst in the form of a catalytic distillation structure. The etherification is that described in U.S. Pat. No. 4,336,407 which is incorporated herein by reference. Generally the size of the particles of resin are such that a fine mesh such as a cloth container is preferred. Such a container and catalytic distillation structure are disclosed in U.S. Pat. No. 4,443,559 which is incorporated herein by reference and is shown to comprises a fiber glass cloth belt with a plurality of pockets containing the resin catalyst. The cloth belt is wound with demister wire to make the distillation structure.

The unreacted methanol, $C_5$'s, and hydrogen are taken overheads via outlet 5 and passed through condenser 13 where the condensible materials are condensed and then collected via line 4 in accumulator-separator 11. A third set of inert distillation structures 15 is optionally position above the second reaction distillation zone 12. The light incondensibles, including the hydrogen are removed from the accumulator via line 3. Liquid is removed form the separator via line 9 with a portion being recycled to the column 10 via line 6 as reflux.

The TAME is not generally separated from the heavier components, but all are used directly as octane blending stocks.

The invention claimed is:

1. A process for the treatment of a light cracked naphtha stream comprising isoamylene comprising the steps of:
  (a) feeding said light cracked naphtha stream to a distillation column reactor having a stripping section and two distillation reaction zones in series;
  (b) concurrently feeding a stream containing hydrogen to said distillation column reactor;
  (c) separating a $C_6$ and heavier boiling fraction from said light cracked naphtha in said stripping section while boiling a $C_5$ boiling fraction containing mercaptan and diolefin contaminants up into a first distillation reaction zone;
  (d) concurrently in said distillation reaction zone
    (i) reacting said mercaptans contained within said $C_5$ boiling fraction with a portion of said diolefins contained within said $C_5$ boiling fraction to produce sulfides having a boiling range higher than said $C_5$ boiling fraction;
    (ii) reacting the remainder of said diolefins and any acetylenes contained within said $C_5$ boiling fraction with a portion of said hydrogen to reduce the unsaturation of said diolefins and said acetylenes; and
    (iii) separating said $C_5$ boiling fraction from said sulfides by fractional distillation;

(e) feeding a stream containing methanol to said distillation column reactor to form a methanol/$C_5$ azeotrope in said first distillation reaction zone, said azeotrope having a lower boiling point than said $C_5$ boiling fraction;

(f) boiling said azeotrope up into a second distillation reaction zone wherein a portion of the isoamylenes contained within said azeotrope react with a portion of the methanol contained within said azeotrope to form tertiary amyl methyl ether;

(g) removing said tertiary amyl methyl ether, said $C_6$ and heavier boiling fraction and said sulfides from said distillation column reactor as bottoms.

2. The process according to claim 1 wherein any nitrogen containing compounds within said $C_5$ fraction are removed with said bottoms.

3. A process according to claim 1 for the production of tertiary amyl methyl ether wherein said first distillation reaction zone comprises a hydrogenation catalyst in the form of a catalytic distillation structure and said second distillation reaction zone comprises an acid cation exchange resin in the form of a catalytic distillation structure.

4. The process according to claim 1 wherein a portion of said methanol is fed above the second distillation reaction zone.

* * * * *